(12) United States Patent
Nakamuta et al.

(10) Patent No.: US 6,794,398 B1
(45) Date of Patent: Sep. 21, 2004

(54) PREVENTIVE/REMEDIES FOR LIVER DISEASES

(75) Inventors: Makoto Nakamuta, Fukuoka (JP);
Hajime Nawata, Fukuoka (JP);
Masayoshi Uehata, Tokyo (JP)

(73) Assignee: Mitsubishi Pharma Corporation, Osaka (JP)

(*) Notice: Subject to any disclaimer, the term of this patent is extended or adjusted under 35 U.S.C. 154(b) by 0 days.

(21) Appl. No.: 09/959,441

(22) PCT Filed: Apr. 27, 2000

(86) PCT No.: PCT/JP00/02797

§ 371 (c)(1),
(2), (4) Date: Mar. 6, 2002

(87) PCT Pub. No.: WO00/64478

PCT Pub. Date: Nov. 2, 2000

(30) Foreign Application Priority Data

Apr. 27, 1999 (JP) .......................................... 11/120624

(51) Int. Cl.$^7$ ......................... A61K 31/53; A61K 31/44;
C07D 213/62; C07D 213/72; C07D 217/22

(52) U.S. Cl. ....................... 514/352; 514/241; 514/242;
514/243; 514/245; 514/256; 514/258; 546/143;
546/256; 546/261; 546/264; 546/272; 546/275;
546/309; 546/297

(58) Field of Search ................................ 514/352, 241,
514/242, 243, 245, 256, 258; 546/143,
256, 261, 264, 272, 275, 309, 297

(56) References Cited

U.S. PATENT DOCUMENTS

| | | | |
|---|---|---|---|
| 4,997,834 A | * | 3/1991 | Muro et al. ............... 514/227.8 |
| 5,906,819 A | | 5/1999 | Kaibuchi et al. |
| 6,218,410 B1 | * | 4/2001 | Uehata et al. .............. 514/352 |

FOREIGN PATENT DOCUMENTS

| | | | |
|---|---|---|---|
| EP | 0 370 498 | * | 5/1990 |
| EP | 0 956 865 A1 | | 11/1999 |
| JP | 63-185921 | | 8/1988 |
| JP | 5-97834 | | 4/1993 |
| JP | 8-67637 | | 3/1996 |
| JP | 10-113187 | | 5/1998 |
| JP | 10-201480 | | 8/1998 |
| WO | 95/28387 | * | 10/1995 |
| WO | 98/06433 | | 2/1998 |

OTHER PUBLICATIONS

Uehata, Nature, vol. 389, pp890–894, Oct. 30, 1997.*

Sugimoto, Rie et al., "P160ROCK–Specific Inhibitor, Y–27632, Suppresses Hepatic Fibrosis Induced Bydimethylnitrosamine In Rats", Hepatology, vol. 30, No. 4, Part 2, p. 489A, Oct. 1999, XP009016968, 50th Annual Meeting and Postgraduate Courses of the American Association for the Study of Liver Diseases; Dallas, Texas, USA; Nov. 5–9, 1999, ISSN: 0270–9139.

Kawada, Norifumi et al., "Rock Inhibitor, Y–27632, Blocks Stellate Cell Contraction and Attenuates Portal Vein Constriction Induced By Endothelin–1", Hepatology, vol. 30, No. 4, Part 2, p. 235A, Oct. 1999, XP009016967, 50th Annual meeting and Postgraduate Courses of the American Association for the Study of Liver Diseases: Dallas, Texas, USAI Nov. 5–9, 1999 ISSN 0903–1936.

Hal F. Yee, Jr., "Rho Directs Activation–Associated Changes in Rat Hepatic Stellate Cell Morphology Via Regulation of the Actin Cytoskeleton", Hepatology, 28, pp. 843–850 (1998).

Kazuyuki Itoh, "An essential part for Rho–associated kinase in the transcellular invasion of tumor cells", Nature Medicine, 5(2), pp. 221–225 (Feb. 1999).

English Abstract of JP 10–201480 A.

English Abstract of JP 63–185921 A.

English Abstract of JP 5–97834 A.

English Abstract of JP 8–67637 A.

Norifumi Kawada et al., "ROCK Inhibitor Y–27632 Attenuates Stellate Cell Contraction and Portal Pressure Increase Induced by Endothelin–1", Biochem Biophys. Res. Commun., 266, pp. 296–300 (1999).

Takuya Genda et al., Cell Motility Mediated by Rho and Rho–Associated Protein Kinase Plays a Critical Role in Intrahepatic Metastasis of Human Hepatocellular Carcinoma, Hepatology, 30, pp. 1027–1036 (1999).

Masaki Kato, "Role of Rho small GTP binding protein in the regulation of actin cytoskeleton in hepatic stellate cells", J. Hepatology, 31, pp. 91–99 (1999).

Yee, H. F., Jr., "Rho Directs Activation–Associated Changes in Rat Hepatic Stellate Cell Morphology Via Regulation of the Actin Cytoskelton", HEPATOLOGY, 28, pp. 843–850, (1998).

(List continued on next page.)

*Primary Examiner*—D. Margaret Seaman
(74) *Attorney, Agent, or Firm*—Wenderoth, Lind & Ponack, L.L.P.

(57) ABSTRACT

The invention provides an agent for the prophylaxis and treatment of liver disease and an activation inhibitor of hepatic stellate cells, which contains a compound having a Rho kinase inhibitory activity. The compound having a Rho kinase inhibitory activity, such as (+)-trans-4-(1-aminoethyl)-1-(4-pyridylcarbamoyl)cyclohexane, is useful for the prophylaxis and treatment of liver diseases, such as hepatitis, hepatic fibrosis, hepatic cirrhosis, hepatic cancer and the like, because it has various actions, such as a superior inhibitory action on the activation of hepatic stellate cell, suppressive action on hepatic fibrogenesis in liver tissues and the like.

9 Claims, 2 Drawing Sheets

OTHER PUBLICATIONS

Itoh, K. et al., "An Essential Part for Rho–Associated Kinase in the Transcellular Invasion of Tumor Cells", Nature Medicine, 5(2), pp. 221–225, Feb. 1999.

Kawada, N., et al., "ROCK Inhibitor Y–27632 Attenuates Stellate Cell Contraction and Portal Pressure Increase Induction by Endothelin–1", Biochem. Biophys. Res. Commun., 266, pp. 296–300, (1999).

Genda, T., et al., "Cell Motility Mediated by Rho and Rho–associated Protein Kinase Plays a Critical Role in Intrahepatic Metastasis of Human Hepatocellular Carcinoma", HEPATOLOGY, 30, pp. 1027–1036, (1999).

Kato M., "Role of Rho Small GTP Binding Protein in the Regulation of Actin Cytoskelton in Hepaticstellate Cells", J. Hepatology, 31, pp. 91–99, (1991).

* cited by examiner

PREVENTIVE/REMEDIES FOR LIVER DISEASES

This application is a 371 of PCT/JP00/02797 filed Apr. 27, 2000.

TECHNICAL FIELD

The present invention relates to an agent for the prophylaxis and treatment of liver disease. More specifically, the present invention relates to an agent for the prophylaxis and treatment of liver diseases, which agent comprises a compound having a Rho kinase inhibitory activity, and most particularly, the present invention relates to an agent for the prophylaxis and treatment of liver diseases caused by the activation of hepatic stellate cells.

BACKGROUND ART

Liver diseases are caused by various factors, such as virus infection, excessive intake of alcohol, bilharziasis and the like. These initial etiologic factors cause gradual replacement of liver parenchyma with connective tissues, leading to fibrogenesis in progress. The progress of fibrogenesis in the liver inhibits hemodynamics, and impairs the process of liver regeneration, making the disease state of liver failure irreversible, which often results in transition to hepatic cirrhosis and hepatic cancer.

The hepatic stellate cell (also called fat storing cell) is a major cell that produces extracellular matrix both in normal liver and liver with advanced fibrogenesis. In a general state, the hepatic stellate cell is supplied as a vitamin A storage site. This cell is in a resting state, scarcely shows a proliferation acticity, and is limited to be an element to constitute connective tissues. In a wounded liver and a fibrogenetic liver, however, the hepatic stellate cell loses lipid droplet thereof and changes to a cell such as myofibroblast. This myofibroblast-like cell is an "activated" cell exhibiting a high proliferation acticity, and synthesizes a large amount of collagen and other extracellular matrix proteins, and expresses smooth muscle type α-actin and desmin. Therefore, the hepatic stellate cell is considered to play a major role in fibrogenesis of the liver, and further in the etiology of of hepatic fibrosis (Shimizu, I. et. al., Gut 44(1), 127–136 (1999)).

Accordingly, a substance that inhibits activation of hepatic stellate cell is considered to be effective for the prophylaxis and treatment of fibrogenesis of the liver, which is caused by the activation of hepatic stellate cell.

As a low molecular weight compound having an inhibitory action on the activation of hepatic stellate cell, only a histone deacetylase inhibitor represented by trichostatin and estradiol have been heretofore reported (JP-A-10-114681, Shimizu, I. et al., ibid.).

In WO98/06433, compounds of the formula (I) to be mentioned later and certain isoquinolinesulfonamide derivatives are described as compounds having a Rho kinase inhibitory activity, and as compounds having a Rho kinase inhibitory activity, is isoquinoline derivatives have also been reported (Naunyn-Schmiedeberg's Archives of Pharmacology 385(1) Suppl., R219, 1998).

A compound having a Rho kinase inhibitory activity is described in WO98/06433 as being widely useful as a therapeutic agent of hypertension, a therapeutic agent of angina pectoris, a cerebrovascular spasm suppressant, a therapeutic agent of asthma, a therapeutic agent of peripheral circulatory disturbance, a premature delivery preventive, a therapeutic agent of arterial sclerosis, an anticancer drug, an anti-inflammatory agent, an immunosuppressant, a therapeutic agent of autoimmune diseases, an anti-AIDS agent, a therapeutic agent of osteoporosis, a therapeutic agent of retinopathy, a cerebral function improver, a contraceptive drug, and a gastrointestinal tract infection preventive. However, WO98/06433 does not contain a description of its usefulness as an inhibitor of the activation of hepatic stellate cells or an agent for the prophylaxis and treatment of liver diseases, or a description to suggest such effect.

Furthermore, the compound of the formula (I) has been already known to be useful as an agent for the prophylaxis and treatment of disorders of circulatory organs such as coronary, cerebral, renal, peripheral artery and the like (e.g., a therapeutic agent of hypertension, a therapeutic agent of angina pectoris, a therapeutic agent of renal and peripheral circulation disorder, a suppressive agent of cerebrovascular contraction and the like), which is potent and long lasting, and also as a therapeutic agent of asthma (JP-A-62-89679, JP-A-3-218356, JP-A-4-273821, JP-A-5-194401, JP-A-6-41080 and WO95/28387).

The isoquinolinesulfonamide derivative described in the above-mentioned WO98/06433 is known to be effective as a vasodilating agent, a therapeutic agent of hypertension, a cerebral function improver, an anti-asthma agent, a heart protecting agent, a platelet aggregation inhibitor, a therapeutic agent of neurologic manifestation, an anti-inflammatory agent, an agent for the prevention and treatment of hyperviscosity syndrome, a therapeutic agent of glaucoma, a diminished tension agent, a motor paralysis improver of cerebral thorombosis, an agent for prevention and treatment of virus infection and transcriptional control factor inhibitor (JP-A-57-200366, JP-A-61-227581, JP-A-2-256617, JP-A-4-264030, JP-A-6-56668, JP-A-6-80569, JP-A-6-293643, JP-A-7-41424, JP-A-7-277979, WO97/23222, JP-A-9-227381, JP-A-10-45598 and JP-A-10-87491).

Moreover, the isoquinoline derivative described in the above-mentioned publication (Naunyn-Schmiedeberg's Archives of Pharmacology 385(1) Suppl., R219, 1998) is known to be useful as an agent for the prevention and treatment of brain tissue disorder due to vasospasm (WO97/28130). However, usefulness of the compounds having a Rho kinase inhibitory activity as activators of hepatic stellate cells or an agent for the prophylaxis and treatment of liver diseases is not disclosed, and there is no description suggestive of such usefulness.

DISCLOSURE OF THE INVENTION

The present invention intends to solve the above-mentioned problems relating to liver diseases, particularly fibrogenesis of the liver, and aims at providing an agent for the prophylaxis and treatment of liver diseases and an activation inhibitor of hepatic stellate cells. In other words, the present invention aims at providing an agent for the prophylaxis and treatment of hepatitis, hepatic fibrosis, hepatic cirrhosis, hepatic cancer and the like.

The present inventors have conducted intensive studies in an attempt to solve the above-mentioned problems and found that a compound having a Rho kinase inhibitory activity inhibits activation of hepatic stellate cells and suppresses hepatic fibrogenesis in liver tissues, and that the compound is useful as an activation inhibitor of hepatic stellate cells and for the prophylaxis and treatment of liver diseases such as hepatitis, hepatic fibrosis, hepatic cirrhosis, hepatic cancer and the like, which resulted in the completion of the present invention.

Accordingly, the present invention provides the following.

(1) An agent for the prophylaxis and treatment of liver disease, which comprises a compound having a Rho kinase inhibitory activity.

(2) The agent for the prophylaxis and treatment: of liver disease of (1) above, wherein the compound having a Rho kinase inhibitory activity is an amide compound of the following formula (I)

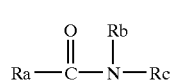
(I)

wherein

Ra is a group of the formula

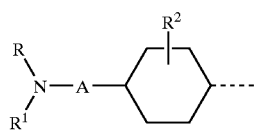
(a)

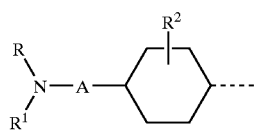
(b)

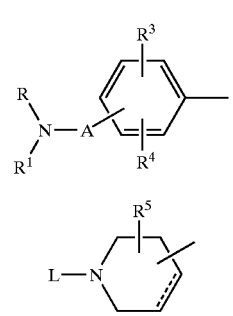
(c)

in the formulas (a) and (b),

R is hydrogen, alkyl, or cycloalkyl, cycloalkylalkyl, phenyl or aralkyl, which optionally has a substituent on the ring, or a group of the formula

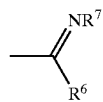
(d)

wherein $R^6$ is hydrogen, alkyl or formula: $-NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

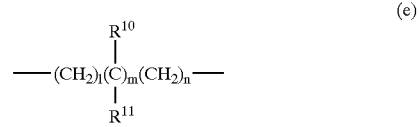
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

(f)

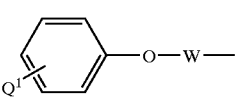
(g)

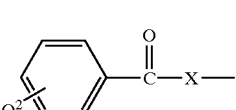
(h)

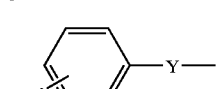
(i)

wherein B is hydrogen, alkyl, alkoxy, aralkyl, aralkyloxy, aminoalkyl, hydroxyalkyl, alkanoyloxy-alkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4, 5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(3) The agent for the prophylaxis and treatment of liver disease of (1) or (2) above, wherein the compound having a Rho kinase inhibitory activity is an amide compound of the following formula (I')

$$Ra'-\overset{O}{\underset{\|}{C}}-\overset{Rb}{\underset{|}{N}}-Rc \qquad (I')$$

wherein
Ra' is a group of the formula $$\begin{array}{c} R' \\ \diagdown \\ N-A-\text{(cyclohexane with } R^2\text{)} \\ / \\ R^1 \end{array} \qquad (a')$$

$$\begin{array}{c} R' \\ \diagdown \\ N-A-\text{(aromatic ring with } R^3, R^4\text{)} \\ / \\ R^1 \end{array} \qquad (b')$$

wherein
R' is hydrogen, alkyl, or cycloalkyl, cycloalkylalkyl, phenyl or aralkyl, which optionally has a substituent on the ring,
$R^1$ is hydrogen, alkyl, or cycloalkyl, cycloalkylalkyl, phenyl or aralkyl, which optionally has a substituent on the ring, or
R' and $R^1$ in combination form, together with the adjacent nitrogen atom, a group forming a heterocycle optionally having, in the ring, oxygen atom, sulfur atom or optionally substituted nitrogen atom,
$R^2$ is hydrogen or alkyl,
$R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and
A is a group of the formula $$-(CH_2)_l(\underset{\underset{R^{11}}{|}}{\overset{\overset{R^{10}}{|}}{C}})_m(CH_2)_n- \qquad (e)$$

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3,
Rb is a hydrogen, an alkyl, an aralkyl, an aminoalkyl or a mono- or dialkylaminoalkyl; and
Rc is an optionally substituted heterocycle containing nitrogen,
an isomer thereof and/or a pharmaceutically acceptable acid addition salt thereof.
(4) The agent for the prophylaxis and treatment of liver disease of (1) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.
(5) The agent for the prophylaxis and treatment of liver disease of (1) above, wherein the compound having a Rho kinase inhibitory activity is (+)-trans-4-(1-aminoethyl)-1-(4-pyridylcarbamoyl)cyclohexane and/or a pharmaceutically acceptable acid addition salt thereof.
(6) The agent for the prophylaxis and treatment of liver disease of any of (1) to (5) above, wherein the liver disease is caused by activation of hepatic stellate cell.
(7) The agent for the prophylaxis and treatment of liver disease of any of (1) to (6) above, wherein the liver disease is at least one selected from the group consisting of hepatitis, hepatic fibrosis, hepatic cirrhosis and hepatic cancer.
(8) An activation inhibitor of hepatic stellate cells, which comprises a compound having a Rho kinase inhibitory activity.
(9) The activation inhibitor of hepatic stellate cells of (8) above, wherein the compound having a Rho kinase inhibitory activity is an amide compound of the formula (I), particularly a compound of the formula (I'), an isomer thereof and/or a pharmaceutically acceptable acid addition salt thereof.
(10) The activation inhibitor of hepatic stellate cells of (8) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.
(11) The activation inhibitor of hepatic stellate cells of (8) above, wherein the compound having a Rho kinase inhibitory activity is (+)-trans-4-(1-aminoethyl)-1-(4-pyridylcarbamoyl)-cyclohexane and/or a pharmaceutically acceptable acid addition salt thereof.
(12) A pharmaceutical composition for the prophylaxis and treatment of liver disease, which comprises a compound having a Rho kinase inhibitory activity and a pharmaceutically acceptable carrier.
(13) The pharmaceutical composition for the prophylaxis and treatment of liver disease of (12) above, wherein the compound having a Rho kinase inhibitory activity is an amide compound of the formula (I), particularly a compound of the formula (I'), an isomer thereof and/or a pharmaceutically acceptable acid addition salt thereof.
(14) The pharmaceutical composition for the prophylaxis and treatment of liver disease of (12) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b)pyridin-4-yl)-4-l(1-aminoethyl)benzamide, and/or a pharmaceutically acceptable acid addition salt thereof.
(15) The pharmaceutical composition for the prophylaxis and treatment of liver disease of (12) above, wherein the compound having a Rho kinase inhibitory activity is (+)-trans-4-(1-aminoethyl)-1-(4-pyridylcarbamoyl)

cyclohexane and/or a pharmaceutically acceptable acid addition salt thereof.

(16) The pharmaceutical composition for the prophylaxis and treatment of liver disease of any of (12) to (15) above, wherein the liver disease is caused by activation of hepatic stellate cell.

(17) The pharmaceutical composition for the prophylaxis and treatment of liver disease of any of (12) to (16) above, wherein the liver disease is at least one selected from the group consisting of hepatitis, hepatic fibrosis, hepatic cirrhosis and hepatic cancer.

(18) A method of the prophylaxis and treatment of liver disease, which comprises administering an effective amount of a compound having a Rho kinase inhibitory activity to a patient.

(19) The method of the prophylaxis and treatment of liver disease of (18) above, wherein the compound having a Rho kinase inhibitory activity is an amide compound of the formula (I), particularly a compound of the formula (I'), an isomer thereof and/or a pharmaceutically acceptable acid addition salt thereof.

(20) The method of the prophylaxis and treatment of liver disease of (18) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

(21) The method of the prophylaxis and treatment of liver disease of (18) above, wherein the compound having a Rho kinase inhibitory activity is a (+)-trans-4-(1-aminoethyl)-1-(4-pyridylcarbamoyl)cyclohexane, and/or a pharmaceutically acceptable acid addition salt thereof.

(22) The method of the prophylaxis and treatment of liver disease of any of (18) to (21) above, wherein the liver disease is caused by activitation of hepatic stellate cell.

(23) The method of the prophylaxis and treatment of liver disease of any of (18) to (22) above, wherein the liver disease is at least one selected from the group consisting of hepatitis, hepatic fibrosis, hepatic cirrhosis and hepatic cancer.

(24) Use of a compound having a Rho kinase inhibitory activity for the production of an agent for the prophylaxis and treatment of liver disease.

(25) The use of (24) above, wherein the compound having a Rho kinase inhibitory activity is an amide compound of the following formula (I), particularly a compound of the formula (I'), an isomer thereof and/or a pharmaceutically acceptable acid addition salt thereof.

(26) The use of (24) above, wherein the compound having a Rho kinase inhibitory activity is a compound selected from the group consisting of (+)-trans-4- (1-aminoethyl)-1-(4-pyridylcarbamoyl)-cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

(27) The use of (24) above, wherein the compound having a Rho kinase inhibitory activity is a (+)-trans-4-(1-aminoethyl)-1-(4-pyridylcarbamoyl)cyclohexane, and/or a pharmaceutically acceptable acid addition salt thereof.

(28) The use of any of (24) to (27), wherein the liver disease is caused by activation of hepatic stellate cell.

(29) The use of any of (24) to (28), wherein the liver disease is at least one selected from the group consisting of hepatitis, hepatic fibrosis, hepatic cirrhosis and hepatic cancer.

(30) A commercial package comprising a pharmaceutical composition for the prophylaxis and treatment of liver disease of any of (12) to (17) above, and a written matter associated therewith, the written matter stating that the pharmaceutical composition can or should be used for the prophylaxis and treatment of liver disease.

DETAILED DESCRIPTION OF THE INVENTION

Figure 1:
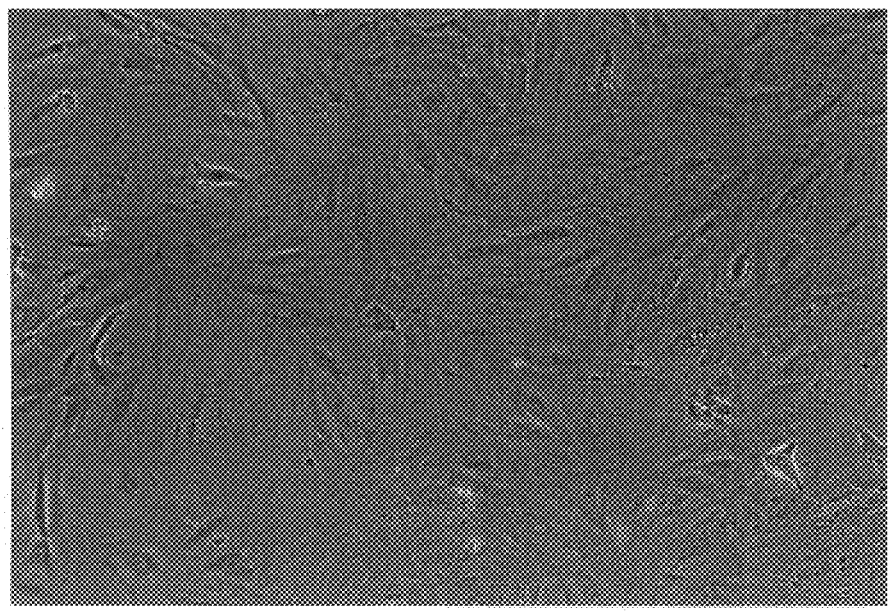
FIG. 1 is a phase contrast microscopic photograph of hepatic stellate cells without Y-27632 [Y-27632: (+)-trans-4-(1-aminoethyl)-1-(4-pyridylcarbamoyl)cyclohexane 2HCl·H$_2$O].

In the present invention, by the "activation" of hepatic stellate cell is meant a state associated with increased synthesis of collagen type I and type III, cell proliferation, expression of smooth muscle type α-actin and the like in the liver. Morphologically, non-active type cell has a spindle like shape with dendroidal protrusions. On the other hand, activated hepatic stellate cells lose lipid droplet thereof and change into cells with an extended shape of, for example, myofibroblast.

Hepatitis is divided into virus hepatitis, toxic hepatitis, autoimmune hepatitis and the like, and into acute hepatitis and chronic hepatitis according to the mode of progress. The hepatitis in the present invention encompasses any type irrespective of the cause thereof, as long as it provides degenerative findings in hepatocytes due to the factors such as activation of hepatic stellate cell and the like.

In addition, the hepatic fibrosis, hepatic cirrhosis and hepatic cancer in the present invention encompass any type caused by various factors such as activation of hepatic stellate cell and the like.

In the present invention, Rho kinase means serine/threonine kinase activated along with the activation of Rho. For example, ROKα (ROCKII: Leung, T. et al, J. Biol. Chem., 270, 29051–29054, 1995), p160 ROCK (ROKβ, ROCK-I: Ishizaki, T. et al, The EMBO J., 15(8), 1885–1893, 1996) and other proteins having a serine/threonine kinase activity are exemplified.

The compound having a Rho kinase inhibitory activity, which is used as an active ingredient in the present invention, may be any as long as it has a Rho kinase inhibitory activity.

Specifically, there are mentioned amide compound, isoquinolinesulfonamide derivative and isoquinoline derivative described in the above-mentioned WO98/06433 and WO97/28130.

As the aforementioned amide compound, for example, a compound of the above-mentioned formula (I), particularly a compound of the formula (I'), are used. As the aforementioned isoquinolinesulfonic acid derivative, fasudil hydrochloride (hexahydro-1-(5-isoquinolinesulfonyl)-1H-1,4-diazepine monohydrochloride] and the like are used. As the aforementioned isoquinoline derivative, hexahydro-1-[(4-methyl-5-isoquinolinyl)sulfonyl]-1H-1,4-diazepine dihydrochloride, (S)-(+)-hexahydro-2-methyl-1-[(4-methyl-5-isoquinolinyl),sulfonyl]-1H-1,4-diazepine hydrochloride, hexahydro-7-methyl-1-[(4methyl-5-isoquinolinyl)sulfonyl]-1H-1,4diazepine dihydrochloride, hexahydro-5-methyl-1-[(4-methyl-5-isoquinolinyl)sulfonyl]-1H-1,4-diazepine dihydrochloride, hexahydro-2-methyl-1-[(4methyl-5-isoquinolinyl)sulfonyl]-1H-1,4-diazepine hydrochloride, (R)-(−)-hexahydro-2-methyl-1-[(4-methyl-5-isoquinolinyl)sulfonyl]-1H-1,4-diazepine hydrochloride, (R)-(+)-hexahydro-5-methyl-1-[(4-methyl-5-isoquinolinyl)sulfonyl]-1H-1,4-diazepine hydrochloride and the like are used.

Preferably, an amide compound of the formula (I), particularly preferably an amide compound of the formula (I'), is used.

In the present invention, one kind of a compound having a Rho kinase inhibitory activity may be used alone, or, where necessary, several kinds may be concurrently used.

In the present specification, each symbol of the formulas (I) and (I') is defined as follows.

Alkyl at R, R' and $R^1$ is linear or branched alkyl having 1 to 10 carbon atoms, which is exemplified by methyl, ethyl, propyl, isopropyl, butyl, isobutyl, sec-butyl, tert-butyl, pentyl, hexyl, heptyl, octyl, nonyl, decyl and the like, with preference given to alkyl having 1 to 4 carbon atoms.

Cycloalkyl at R, R' and $R^1$ has 3 to 7 carbon atoms and is exemplified by cyclopropyl, cyclobutyl, cyclopentyl, cyclohexyl, cycloheptyl and the like.

Cycloalkylalkyl at R, R' and $R^1$ is that wherein the cycloalkyl moiety is the above-mentioned cycloalkyl having 3 to 7 carbon atoms and the alkyl moiety is linear or branched alkyl having 1 to 6 carbon atoms (e.g., methyl, ethyl, propyl, isopropyl, butyl, pentyl, hexyl and the like), which is exemplified by cyclopropylmethyl, cyclobutylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl, cyclopropylbutyl, cyclopentylbutyl, cyclohexylbutyl, cycloheptylbutyl, cyclopropylhexyl, cyclopentylhexyl, cyclohexylhexyl, cycloheptylhexyl and the like.

Aralkyl at R, R' and $R^1$ is that wherein alkyl moiety is alkyl having 1 to 4 carbon atoms and is exemplified by phenylalkyl such as benzyl, 1-phenylethyl, 2-phenylethyl, 3-phenylpropyl, 4-phenylbutyl and the like.

The substituent of optionally substituted cycloalkyl, cycloalkylalkyl, phenyl and aralkyl on the ring at R, R' and $R^1$ is halogen (e.g., chlorine, bromine, fluorine and iodine), alkyl (same as alkyl at R, R' and $R^1$), alkoxy (linear or branched alkoxy having 1 to 6 carbon atoms, such as methoxy, ethoxy, propoxy, isopropoxy, butoxy, isobutoxy, sec-butoxy, tert-butoxy, pentyloxy, hexyloxy and the like), aralkyl (same as aralkyl at R, R' and $R^1$) or haloalkyl (alkyl at R, R' and $R^1$ which is substituted by 1–5 halogen, and exemplified by fluoromethyl, difluoromethyl, trifluoromethyl, 2,2,2-trifluoroethyl, 2,2,3,3,3-pentafluoropropyl and the like), nitro, amino, cyano, azide and the like.

The group formed by R and $R^1$ or R' and $R^1$ in combination together with the adjacent nitrogen atom, which forms a heterocycle optionally having, in the ring, oxygen atom, sulfur atom or optionally substituted nitrogen atom is preferably a 5 or 6-membered ring and bonded ring thereof. Examples thereof include 1-pyrrolidinyl, piperidino, 1-piperazinyl, morpholino, thiomorpholino, 1-imidazolyl, 2,3-dihydrothiazol-3-yl and the like. The substituent of the optionally substituted nitrogen atom is exemplified by alkyl, aralkyl, haloalkyl and the like. As used herein, alkyl, aralkyl and haloalkyl are as defined for R, R' and $R^1$.

Alkyl at $R^2$ is as defined for R, R' and $R^1$.

Halogen, alkyl, alkoxy and aralkyl at $R^3$ and $R^4$ are as defined for R, R' and $R^1$.

Acyl at $R^3$ and $R^4$ is alkanoyl having 2 to 6 carbon atoms (e.g., acetyl, propionyl, butyryl, valeryl, pivaloyl and the like), benzoyl or phenylalkanoyl wherein the alkanoyl moiety has 2 to 4 carbon atoms (e.g., phenylacetyl, phenylpropionyl, phenylbutyryl and the like).

Alkylamino at $R^3$ and $R^4$ is that wherein the alkyl moiety is linear or branched alkyl having 1 to 6 carbon atoms. Examples thereof include methylamino, ethylamino, propylamino, isopropylamino, butylamino, isobutylamino, sec-butylamino, tert-butylamino, pentylamino, hexylamino and the like.

Acylamino at $R^3$ and $R^4$ is that wherein acyl moiety is alkanoyl having 2 to 6 carbon atoms, benzoyl, phenylalkanoyl wherein the alkanoyl moiety has 2 to 4 carbon atoms and the like, which is exemplified by acetylamino, propionylamino, butyrylamino, valerylamino, pivaloylamino, benzoylamino, phenylacetylamino, phenylpropionylamino, phenylbutyrylamino and the like.

Alkylthio at $R^3$ and $R^4$ is that wherein the alkyl moiety is linear or branched alkyl having 1 to 6 carbon atoms, which is exemplified by methylthio, ethylthio, propylthio, isopropylthio, butylthio, isobutylthio, sec-butylthio, tert-butylthio, pentylthio, hexylthio and the like.

Aralkyloxy at $R^3$ and $R^4$ is that wherein the alkyl moiety is alkyl having 1 to 4 carbon atoms, which is exemplified by benzyloxy, 1-phenylethyloxy, 2-phenylethyloxy, 3-phenylpropyloxy, 4-phenylbutyloxy and the like.

Aralkylthio at $R^3$ and $R^4$ is that wherein the alkyl moiety is alkyl having 1 to 4 carbon atoms, which is exemplified by benzylthio, 1-phenylethylthio, 2-phenylethylthio, 3-phenylpropylthio, 4-phenylbutylthio and the like.

Alkoxycarbonyl at $R^3$ and $R^4$ is that wherein the alkoxy moiety is linear or branched alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Mono- or dialkylcarbamoyl at $R^3$ and $R^4$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

Alkoxy at $R^5$ is as defined for R, R' and $R^1$.

Alkoxycarbonyloxy at $R^5$ is that wherein the alkoxy moiety is linear or branched alkoxy having 1 to 6 carbon atoms, which is exemplified by methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, hexyloxycarbonyloxy and the like.

Alkanoyloxy at $R^5$ is that wherein the alkanoyl moiety is alkanoyl having 2 to 6 carbon atoms, which is exemplified by acetyloxy, propionyloxy, butyryloxy, valeryloxy, pivaloyloxy and the like.

Aralkyloxycarbonyloxy at $R^5$ is that wherein the aralkyl moiety is aralkyl having $C_1$–$C_4$ alkyl, which is exemplified by benzyloxycarbonyloxy, 1-phenylethyloxycarbonyloxy, 2-phenylethyloxycarbonyloxy, 3-phenylpropyloxycarbonyloxy, 4-phenylbutyloxycarbonyloxy and the like.

Alkyl at $R^6$ is as defined for R, R' and $R^1$; alkyl at $R^8$ and $R^9$ is as defined for R, R' and $R^1$; and aralkyl at $R^8$ and $R^9$ is as defined for R, R' and $R^1$.

Alkyl at $R^7$ is as defined for R, R' and $R^1$ and aralkyl at $R^7$ is as defined for R, R' and $R^1$.

The group formed by $R^6$ and $R^7$ in combination, which forms a heterocycle optionally having, in the ring, oxygen atom, sulfur atom or optionally substituted nitrogen atom, is imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl or optionally substituted benzoimidazol-2-yl, benzothiazol-2-yl, benzoxazol-2-yl and the like having a substituent such as halogen, alkyl, alkoxy, haloalkyl, nitro, amino, phenyl, aralkyl and the like. As used herein, halogen, alkyl, alkoxy, haloalkyl and aralkyl are as defined for R, R' and $R^1$.

The substituent of the above-mentioned optionally substituted nitrogen atom is exemplified by alkyl, aralkyl, haloalkyl and the like. As used herein, alkyl, aralkyl and haloalkyl are as defined for R, R' and $R^1$.

Hydroxyalkyl at $R^{10}$ and $R^{11}$ is linear or branched alkyl having 1 to 6 carbon atoms which is substituted by 1 to 3 hydroxy, which is exemplified by hydroxymethyl, 2-hydroxyethyl, 1-hydroxyethyl, 3-hydroxypropyl, 4-hydroxybutyl and the like.

Alkyl at $R^{10}$ and $R^{11}$ is as defined for R, R' and $R^1$; haloalkyl and alkoxycarbonyl at $R^{10}$ and $R^{11}$ are as defined for R, R' and $R^1$; aralkyl at $R^{10}$ and $R^{11}$ is as defined for R, R' and $R^1$.

Cycloalkyl formed by $R^{10}$ and $R^{11}$ in combination is the same as cycloalkyl at R, R' and $R^1$.

Alkyl at L is as defined for R, R' and $R^1$.

Aminoalky at L is a linear or branched alkyl having 1 to 6 carbon atoms, which is substituted by amino, which is exemplified by aminomethyl, 2-aminoethyl, 1-aminoethyl, 3-aminopropyl, 4-aminobutyl, 5-aminopentyl, 6-aminohexyl and the like.

Mono- or dialkylaminoalkyl at L is mono- or di-substituted aminoalkyl with alkyl having 1 to 4 carbon atoms, which is exemplified by methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylaminoethyl and the like.

Carbamoylalkyl at L is linear or branched alkyl having 1 to 6 carbon atoms substituted by carbamoyl, which is exemplified by carbamoylmethyl, 2-carbamoylethyl, 1-carbamoylethyl, 3-carbamoylpropyl, 4-carbamoylbutyl, 5-carbamoylpentyl, 6-carbamoylhexyl and the like.

Phthalimidoalkyl at L is linear or branched alkyl having 1 to 6 carbon atoms, which is substituted by phthalimide. Examples thereof include phthalimidoethyl, 2-phthalimidoethyl, 1-phthalimidoethyl, 3-phthalimidopropyl, 4-phthalimidobutyl, 5-phthalimidopentyl, 6-phthalimidohexyl and the like.

Alkyl at B is as defined for R, R' and $R^1$.
Alkoxy at B is as defined for R, R' and $R^1$,
Aralkyl at B is as defined for R, R' and $R^1$.

Aralkyloxy at B is as defined for $R^3$ and $R^4$.
Aminoalkyl at B is as defined for L.
Hydroxyalkyl at B is as defined for $R^{10}$ and $R^{11}$.

Alkanoyloxyalkyl at B is that wherein linear or branched alkyl having 1 to 6 carbon atoms is substituted by alkanoyloxy having alkanoyl moiety having 2 to 6 carbon atoms, which is exemplified by acetyloxymethyl, propionyloxymethyl, butyryloxymethyl, valeryloxymethyl, pivaloyloxymethyl, acetyloxyethyl, propionyloxyethyl, butyryloxyethyl, valeryloxyethyl, pivaloyloxyethyl and the like.

Alkoxycarbonylalkyl at B is that wherein linear or branched alkyl having 1 to 6 carbon atoms is substituted by alkoxycarbonyl having alkoxy moiety having 1 to 6 carbon atoms, which is exemplified by methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, pentyloxycarbonylmethyl, hexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, sec-butoxycarbonylethyl, tert-butoxycarbonylethyl, pentyloxycarbonylethyl, hexyloxycarbonylethyl and the like.

Halogen at $Q^1$, $Q^2$ and $Q^3$ is as defined for R, R' and $R^1$.
Aralkyloxy at $Q^1$ and $Q^2$ is as defined for $R^3$ and $R^4$.
Alkoxy at $Q^3$ is as defined for R, R' and $R^1$.

Alkylene at W, X and Y is linear or branched alkylene having 1 to 6 carbon atoms, which is exemplified by methylene, ethylene, trimethylene, propylene, tetramethylene, pentamethylene, hexamethylene and the like.

Alkenylene at Y is linear or branched alkenylene having 2 to 6 carbon atoms, which is exemplified by vinylene, propenylene, butenylene, pentenylene and the like.

Alkyl at Rb is as defined for R, R' and $R^1$.
Aralkyl at Rb is as defined for R, R' and $R^1$.
Aminoalkyl at Rb is as defined for L.
Mono- or dialkylaminoalkyl at Rb is as defined for L.

The heterocycle containing nitrogen at Rc is pyridine, pyrimidine, pyridazine, triazine, pyrazole, triazole and the like when it is monocycle, and when it is a condensed ring, it is exemplified by pyrrolopyridine (e.g., 1H-pyrrolo[2,3-b]pyridine, 1H-pyrrolo[3,2-b]pyridine, 1H-pyrrolo[3,4-b]pyridine and the like), pyrazolopyridine (e.g., 1H-pyrazolo[3,4-b]pyridine, 1H-pyrazolo[4,3-b]pyridine and the like), imidazopyridine (e.g., 1H-imidazo[4,5-b]pyridine and the like), pyrrolopyrimidine (e.g., 1H-pyrrolo[2,3-d]pyrimidine, 1H-pyrrolo[3,2-d]pyrimidine, 1H-pyrrolo[3,4-d]pyrimidine and the like), pyrazolopyrimidine (e.g., 1H-pyrazolo[3,4-d]pyrimidine, pyrazolo[1,5-a]pyrimidine, 1H-pyrazolo[4,3-d]pyrimidine and the like), imidazopyrimidine (e.g., imidazo[1,2-a]pyrimidine, 1H-imidazo[4,5-d]pyrimidine and the like), pyrrolotriazine (e.g., pyrrolo[2-a]-1,3,5-triazine, pyrrolo[2,1-f]-1,2,4-triazine), pyrazolotriazine (e.g., pyrazolo[5-a]-1,3,5-triazine and the like), triazolopyridine (e.g., 1H-1,2,3-triazolo[4,5-b]pyridine and the like), triazolopyrimidine (e.g., 1,2,4-triazolo[1,5-a]pyrimidine, 1,2,4-triazolo[4,3-a]pyrimidine, 1H-1,2,3-triazolo[4,5-d]pyrimidine and the like), cinnoline, quinazoline, quinoline, pyridopyridazine (e.g., pyrido[2,3-c]pyridazine and the like), pyridopyrazine (e.g., pyrido[2,3-b]pyrazine and the like), pyridopyrimidine (e.g., pyrido[2,3-d]pyrimidine, pyrido[3,2-d]pyrimidine and the like), pyrimidopyrimidine (e.g., pyrimido[4,5-d]pyrimidine, pyrimido[5,4-d]pyrimidine and the like), pyrazinopyrimidine (e.g., pyrazino[2,3-d]pyrimidine and the like), naphthyridine (e.g., 1,8-naphthyridine and the like), tetrazolopyrimidine (e.g., tetrazolo[1,5-a]pyrimidine and the like), thienopyridine (e.g., thieno[2,3-b]pyridine and the like), thienopyrimidine (e.g., thieno[2,3-d]pyrimidine and the like), thiazolopyridine (e.g., thiazolo[4,5-b]pyridine, thiazolo[5,4-b]pyridine and the like), thiazolopyrimidine (e.g., thiazolo[4,5-d]pyrimidine, thiazolo([5,4-d]pyrimidine and the like), oxazolopyridine (e.g., oxazolo[4,5-b]pyridine, oxazolo[5,4-b]pyridine and the like), oxazolopyrimidine (e.g., oxazolo[4,5-d]pyrimidine, oxazolo[5,4-d]pyrimidine and the like), furopyridine (e.g., furo[2,3-b]pyridine, furo[3,2-b]pyridine and the like), furopyrimidine (e.g., furo[2,3-d]pyrimidine, furo[3,2-d]pyrimidine and the like), 2,3-dihydropyrrolopyridine (e.g., 2,3-dihydro-1H-pyrrolo[2,3-b]pyridine, 2,3dihydro-1H-pyrrolo[3,2-b]pyridine and the like), 2,3-dihydropyrrolopyrimidine (e.g., 2,3-dihydro-1H-pyrrolo[2,3-d]pyrimidine, 2,3-dihydro-1H-pyrrolo[3,2-d]pyrimidine and the like), 5,6,7,8-tetrahydropyrido[2,3-d]pyrimidine, 5,6,7,8-tetrahydro-1,8-naphthyridine, 5,6,7,8-tetrahydroquinoline and the like. When these rings form a hydrogenated aromatic ring, the carbon atom in the ring may be carbonyl and includes, for example, 2,3-dihydro-2-oxopyrrolopyridine, 2,3-dihydro-2,3-dioxopyrrolopyridine, 7,8-dihydro-7-oxo-1,8-naphthyridine, 5,6,7,8-tetrahydro-7-oxo-1,8-naphthyridine and the like.

These rings may be substituted by a substituent such as halogen, alkyl, alkoxy, aralkyl, haloalkyl, nitro, amino, alkylamino, cyano, formyl, acyl, aminoalkyl, mono- or dialkylaminoalkyl, azide, carboxy, alkoxycarbonyl, carbamoyl, mono- or dialkylcarbamoyl, alkoxyalkyl (e.g., methoxymethyl, methoxyethyl, methoxypropyl, ethoxymethyl, ethoxyethyl, ethoxypropyl and the like), optionally substituted hydrazino and the like.

As used herein, the substituent of the optionally substituted hydrazino includes alkyl, aralkyl, nitro, cyano and the like, wherein alkyl and aralkyl are as defined for R, R' and $R^1$ and exemplified by methylhydrazino, ethylhydrazino, benzylhydrazino and the like.

The compound of the formula (I) is exemplified by the following compounds.

(1) 4-(2-pyridylcarbamoyl)piperidine
(2) 1-benzyloxycarbonyl-4-(4-pyridylcarbamoyl)piperidine
(3) 1-benzoyl-4-(4-pyridylcarbamoyl)piperidine
(4) 1-propyl-4-(4-pyridylcarbamoyl)piperidine
(5) 1-[3-(2-(2-thienylmethyl)phenoxy)-2-hydroxypropyl]-4-(4-pyridylcarbamoyl)piperidine
(6) 4-(4-pyridylcarbamoyl)piperidine
(7) 1-benzyl-4-(4-pyridylcarbamoyl)-1,2,5,6-tetrahydropyridine
(8) 3-(4-pyridylcarbamoyl)piperidine
(9) 1-benzyl-3-(4-pyridylcarbamoyl)piperidine
(10) 1-(2-(4-benzyloxyphenoxy)ethyl)-4-(N-(2-pyridyl)-N-benzylcarbamoyl)pyridine
(11) 1-formyl-4-(4-pyridylcarbamoyl)piperidine
(12) 4-(3-pyridylcarbamoyl)piperidine
(13) 1-isopropyl-4-(4-pyridylcarbamoyl)piperidine
(14) 1methyl-4-(4-pyridylcarbamoyl)piperidine
(15) 1-hexyl-4-(4-pyridylcarbamoyl)piperidine
(16) 1-benzyl-4-(4-pyridylcarbamoyl)piperidine
(17) 1-(2-phenylethyl)-4-(4-pyridylcarbamoyl)piperidine
(18) 1-(2-(4-methoxyphenyl)ethyl)-4-(4-pyridylcarbamoyl)piperidine
(19) 1-(2-(4-methoxyphenyl)ethyl)-4-(2-pyridylcarbamoyl)piperidine
(20) 1-(2-(4-chlorophenyl)ethyl)-4-(4-pyridylcarbamoyl)piperidine
(21) 1-diphenylmethyl-4-(2-pyridylcarbamoyl)piperidine
(22) 1-[2-(4-(5-methyl-3-oxo-2,3,4,5-tetrahydropyridazin-6-yl)phenyl)ethyl]-4-(2-pyridylcarbamoyl)piperidine
(23) 1-(4-(4,5-dihydro-2-furyl)phenyl)-4-(4-pyridylcarbamoyl)-piperidine
(24) 1-(2-nitrophenyl)-4-(4-pyridylcarbamoyl)piperidine
(25) 1-(2-aminophenyl)-4-(4-pyridylcarbamoyl)piperidine
(26) 1-nicotinoyl-4-(4-pyridylcarbamoyl)piperidine
(27) 1-isonicotinoyl-4-(4-pyridylcarbamoyl)piperidine
(28) 1-(3,4,5-trimethoxybenzoyl)-4-(4-pyridylcarbamoyl)piperidine
(29) 1-acetyl-4-(4-pyridylcarbamoyl)piperidine
(30) 1-(3-(4-fluorobenzoyl)propyl)-4-(4-pyridylcarbamoyl)piperidine
(31) 1-(3-(4-fluorobenzoyl)propyl)-4-(2-pyridylcarbamoyl)piperidine
(32) 1-(1-(4-hydroxybenzoyl)ethyl)-4-(2-pyridylcarbamoyl)piperidine
(33) 1-(1-(4-benzyloxybenzoyl)ethyl)-4-(2-pyridylcarbamoyl)piperidine
(34) 1-(2-(4-hydroxyphenoxy)ethyl)-4-(2-pyridylcarbamoyl)piperidine
(35) 1-(4-(4-fluorophenyl)-4-hydroxybutyl)-4-(4-pyridylcarbamoyl)piperidine
(36) 1-(1-methyl-2-(4-hydroxyphenyl)-2-hydroxyethyl)-4-(2-pyridylcarbamoyl)piperidine
(37) 1-cinnamyl-4-(2-pyridylcarbamoyl)piperidine
(38) 1-(2-hydroxy-3-phenoxypropyl)-4-(4-pyridylcarbamoyl)piperidine
(39) 1-(2-hydroxy-3-phenoxypropyl)-4-(3-pyridylcarbamoyl)piperidine
(40) 1-(2-hydroxy-3-phenoxypropyl)-4-(2-pyridylcarbamoyl)piperidine
(41) 1-(2-phenylethyl)-4-[N-(2-pyridyl)-N-(2-(N,N-N-dimethylamino)ethyl)carbamoyl]piperidine
(42) 1-benzyloxycarbonyl-4-(2-pyridylcarbamoyl)piperidine
(43) 1-(3-chlorophenyl)carbamoyl-4-(4-pyridylcarbamoyl)piperidine
(44) 4-[N-(2-pyridyl)-N-(2-(N,N-dimethylamino)ethyl)carbamoyl]piperidine
(45) 1-methyl-4-(4-pyridylcarbamoyl)-1,2,5,6-tetrahydropyridine
(46) 1-nicotinoyl-3-(4-pyridylcarbamoyl)piperidine
(47) 1-[2-(4-fluorobenzoyl)ethyl]-4-(4-pyridylcarbamoyl)piperidine
(48) 1-(6-chloro-2methylimidazo[1,2-a]pyridine-3-carbonyl)-4-(4-pyridylcarbamoyl)piperidine
(49) 1-(4-nitrobenzyl)-4-(4-pyridylcarbamoyl)piperidine
(50) 1-hexyl-4-(4-pyridylcarbamoyl)piperidine
(51) 1-benzyloxycarbonyl-4-(2-chloro-4-pyridylcarbamoyl)piperidine
(52) 4-(2-chloro-4-pyridylcarbamoyl)piperidine
(53) 1-(2-chloronicotinoyl)-4-(4-pyridylcarbamoyl)piperidine
(54) 3-(2-chloro-4-pyridylcarbamoyl)piperidine
(55) 1-(4-phthalimidobutyl)-4-(4-pyridylcarbamoyl)piperidine
(56) 1-(3,5-di-tert-butyl-4-hydroxycinnamoyl)-4-(4-pyridylcarbamoyl)piperidine
(57) 1-carbamoylmethyl-4-(4-pyridylcarbamoyl)piperidine
(58) 1-benzyloxycarbonyl-4-(5-nitro-2-pyridylcarbamoyl)piperidine
(59) 4-(5-nitro-2-pyridylcarbamoyl)piperidine
(60) trans-4-benzyloxycarboxamidomethyl-1-(4-pyridylcarbamoyl)-cyclohexane

(61) trans-4-aminomethyl-1-(4-pyridylcarbamoyl)cyclohexane
(62) trans-4-formamidomethyl-1-(4-pyridylcarbamoyl)cyclohexane
(63) trans-4-dimethylaminomethyl-1-(4-pyridylcarbamoyl)cyclohexane
(64) N-benzylidene-trans-(4-pyridylcarbamoyl)cyclohexylmethylamine
(65) trans-4-benzylaminomethyl-1-(4-pyridylcarbamoyl)cyclohexane
(66) trans-4-isopropylaminomethyl-1-(4-pyridylcarbamoyl)cyclohexane
(67) trans-4-nicotinoylaminomethyl-1-(4-pyridylcarbamoyl)cyclohexane
(68) trans-4-cyclohexylaminomethyl-1-(4-pyridylcarbamoyl)cyclohexane
(69) trans-4-benzyloxycarboxamide-1-(4-pyridylcarbamoyl)cyclohexane
(70) trans-4-amino-1-(4-pyridylcarbamoyl)cyclohexane
(71) trans-4-(1-aminoethyl)-1-(4-pyridylcarbamoyl)cyclohexane
(72) trans-4-aminomethyl-cis-2-methyl-1-(4-pyridylcarbamoyl)cyclohexane
(73) (+)-trans-4-(1-benzyloxycarboxamidopropyl)-1-cyclohexanecarboxylic acid
(74) (+)-trans-4-(1-benzyloxycarboxamidopropyl)-1-(4-pyridylcarbamoyl)cyclohexane
(75) (−)-trans-4-(1-benzyloxycarboxamidpropyl)-1-(4-pyridylcarbamoyl)cyclohexane
(76) (+)-trans-4-(1-aminopropyl)-1-(4-pyridylcarbamoyl)cyclohexane
(77) (−)-trans-4-(1-aminopropyl)-1-(4-pyridylcarbamoyl)cyclohexane
(78) (−)-trans-4-(1-benzyloxycarboxamidoethyl)-1-(4-pyridylcarbamoyl)cyclohexane
(79) (+)-trans-4-(1-benzyloxycarboxamidoethyl)-1-(4-pyridylcarbamoyl)cyclohexane
(80) (+)-trans-4-(1-aminoethyl)-1-(4-pyridylcarbamoyl)cyclohexane
(81) (−)-trans-4-(1-aminoethyl)-1-(4-pyridylcarbamoyl)cyclohexane
(82) trans-4-(4-chlorobenzoyl)aminomethyl-1-(4-pyridylcarbamoyl)cyclohexane
(83) trans-4-aminomethyl-1-(2-pyridylcarbamoyl)cyclohexane
(84) trans-4-benzyloxycarboxamidomethyl-1-(2-pyridylcarbamoyl)cyclohexane
(85) trans-4-methylaminomethyl-1-(4-pyridylcarbamoyl)cyclohexane
(86) trans-4-(N-benzyl-N-methylamino)methyl-1-(4-pyridylcarbamoyl)cyclohexane
(87) trans-4-aminomethyl-1-(3-pyridylcarbamoyl)cyclohexane
(88) trans-4-aminomethyl-1-[(3-hydroxy-2-pyridyl)carbamoyl]cyclohexane
(89) trans-4-benzyloxycarboxamidomethyl-1-(3-pyridylcarbamoyl)cyclohexane
(90) trans-4-benzyloxycarboxamidomethyl-1-[(3-benzyloxy-2-pyridyl)carbamoyl]cyclohexane
(91) trans-4-phthalimidomethyl-1-(4-pyridylcarbamoyl)cyclohexane
(92) trans-4-benzyloxycarboxamidomethyl-1-(3-methyl-4-pyridylcarbamoyl)cyclohexane
(93) trans-4-aminomethyl-1-(3-methyl-4-pyridylcarbamoyl)-cyclohexane
(94) 4-(trans-4-benzyloxycarboxamidomethylcyclohexylcarbonyl)amino-2,6-dimethylpyridine-N-oxide
(95) 4-(trans-4-aminomethylcyclohexylcarbonyl)amino-2,6-dimethylpyridine-N-oxide
(96) trans-4-aminomethyl-1-(2-methyl-4-pyridylcarbamoyl)cyclohexane
(97) trans-4-(1-benzyloxycarboxamidoethyl)-1-(4-pyridylcarbamoyl)cyclohexane
(98) trans-4-(1-amino-1-methylethyl)-1-(4-pyridylcarbamoyl)cyclohexane
(99) trans-4-(2-aminoethyl)-1-(4-pyridylcarbamoyl)cyclohexane
(100) trans-4-(2-amino-1-methylethyl)-1-(4-pyridylcarbamoyl)cyclohexane
(101) trans-4-(1-aminopropyl)-1-(4-pyridylcarbamoyl)cyclohexane
(102) trans-4-aminomethyl-trans-1-methyl-1-(4-pyridylcarbamoyl)cyclohexane
(103) trans-4-benzylaminomethyl-cis-2-methyl-1-(4-pyridylcarbamoyl)cyclohexane
(104) trans-4-(1-benzyloxycarboxamide-1-methylethyl)-1-(4-pyridylcarbamoyl)cyclohexane
(105) trans-4-benzyloxycarboxamidomethyl-1-(N-methyl-4-pyridylcarbamoyl)cyclohexane
(106) trans-4-(1-acetamide-1-methylethyl)-1-(4-pyridylcarbamoyl)cyclohexane
(107) trans-N-(6-amino-4-pyrimidyl)-4-aminomethylcyclohexanecarboxamide
(108) trans-N-(1H-pyrrolo[2,3-b]pyridin-4-yl)-4-aminomethylcyclohexanecarboxamide
(109) (+)-trans-N-(1H-pyrrolo[2,3-b]pyridin-4-yl)-4-(1-aminoethyl)cyclohexanecarboxamide
(110) trans-N-(1H-pyrrolo[2,3-b]pyridin-4-yl)-4-(1-amino-1-methylethyl)cyclohexanecarboxamide
(111) trans-N-(1H-pyrazolo[3,4-b]pyridin-4-yl)-4-aminomethylcyclohexanecarboxamide
(112) (+)-trans-N-(1H-pyrazolo[3,4-b]pyridin-4-yl)-4-(1-aminoethyl)cyclohexanecarboxamide
(113) trans-N-(1H-pyrazolo[3,4-b]pyridin-4-yl)-4-(1-amino-1-methylethyl)cyclohexanecarboxamide
(114) (+)-trans-N-(2-amino-4-pyridyl)-4-(1-aminoethyl)cyclohexanecarboxamide
(115) trans-N-(1H-pyrazolo[3,4-d]pyrimidin-4-yl)-4-aminomethylcyclohexanecarboxamide
(116) (+)-trans-N-(1H-pyrazolo[3,4-d]pyrimidin-4-yl)-4-(1-aminoethyl)cyclohexanecarboxamide
(117) trans-N-(1H-pyrazolo[3,4-d]pyrimidin-4-yl)-4-(1-amino-1-methylethyl)cyclohexanecarboxamide
(118) trans-N-(4-pyrimidinyl)-4-aminomethylcyclohexanecarboxamide
(119) trans-N-(3-amino-4-pyridyl)-4-aminomethylcyclohexanecarboxamide
(120) trans-N-(7H-imidazo[4,5-d]pyrimidin-6-yl)-4-aminomethylcyclohexanecarboxamide
(121) trans-N-(3H-1,2,3-triazolo[4,5-d]pyrimidin-7-yl)-4-aminomethylcyclohexanecarboxamide
(122) trans-N-(1-benzyl-1H-pyrazolo[3,4-b]pyridin-4-yl)-4-aminomethylcyclohexanecarboxamide
(123) trans-N-(1H-5-pyrazolyl)-4-aminomethylcyclohexanecarboxamide
(124) trans-N-(1H-pyrazolo[3,4-b]pyridin-4-yl)-4-aminomethylcyclohexanecarboxamide
(125) trans-N-(4-pyridazinyl)-4-aminomethylcyclohexanecarboxamide
(126) trans-N-(7H-pyrrolo[2,3-d]pyrimidin-4-yl)-4-aminomethylcyclohexanecarboxamide
(127) trans-N-(2-amino-4-pyridyl)-4-aminomethylcyclohexanecarboxamide
(128) trans-N-(thieno[2,3-d]pyrimidin-4-yl)-4-aminomethylcyclohexanecarboxamide (129) trans-N-(5- methyl-1,2,4-triazolo[1,5-a]pyrimidin-7-yl)-4-aminomethylcyclohexanecarboxamide
(130) trans-N-(3-cyano-5-methylpyrazolo[1,5-a]pyrimidin-7-yl)-4-aminomethylcyclohexanecarboxamide
(131) trans-N-(1H-pyrazolo[3,4-b]pyridin-4-yl)-4-(1-amino-1-methylethyl)cyclohexanecarboxamide
(132) trans-N-(2-(1-pyrrolidinyl)-4-pyridyl)-4-aminomethylcyclohexanecarboxamide
(133) trans-N-(2,6-diamino-4-pyrimidyl)-4-aminomethylcyclohexanecarboxamide
(134) (+)-trans-N-(7-methyl-1,8-naphthyridin-4-yl)-4-(1-aminoethyl)cyclohexanecarboxamide
(135) trans-N-(1-benzyloxymethylpyrrolo[2,3-b]pyridin-4-yl)-4-aminomethylcyclohexanecarboxamide
(136) (+)-trans-N-(1-methylpyrrolo[2,3-b]pyridin-4-yl)-4-(1-aminoethyl)cyclohexanecarboxamide
(137) trans-N-benzyl-N-(2-benzylamino-4-pyridyl)-4-(1-amino-1-methylethyl)cyclohexanecarboxamide
(138) trans-N-(2-azide-4-pyridyl)-4-aminomethylcyclohexanecarboxamide
(139) trans-N-(2,3-dihydro-1H-pyrrolo[2,3-b]pyridin-4-yl)-4-aminomethylcyclohexanecarboxamide
(140) trans-N-(2,3-dihydro-1H-pyrrolo[2,3-b]pyridin-4-yl)-4-(1-amino-1-methylethyl)cyclohexanecarboxamide
(141-1) trans-N-(2-carboxy-4-pyridyl)-4-aminomethylcyclohexanecarboxamide
(141-2) (R)-(+)-trans-N-(3-bromo-1H-pyrrolo[2,3-b]pyridin-4-yl)-4-(1-aminoethyl)cyclohexanecarboxamide
(142) trans-N-(1H-pyrrolo[2,3-b]pyridin-4-yl)-4-guanidinomethylcyclohexanecarboxamide
(143) trans-N-(1H-pyrazolo[3,4-b]pyridin-4-yl)-4-guanidinomethylcyclohexanecarboxamide
(144) trans-N-(4-pyridyl)-4-guanidinomethylcyclohexanecarboxamide
(145) trans-N-(1-methylpyrrolo[2,3-b]pyridin-4-yl)-4-(guanidinomethyl)cyclohexanecarboxamide
(146) trans-N-(1H-pyrrolo[2,3-b]pyridin-4-yl)-4-(2-imidazolin-2-yl)aminomethylcyclohexanecarboxamide
(147) trans-N-(1-benzyloxymethylpyrrolo[2,3-b]pyridin-4-yl)-4-guanidinomethylcyclohexanecarboxamide
(148) trans-N-(2-amino-4-pyridyl)-4-guanidinomethylcyclohexanecarboxamide
(149) trans-N-(1-benzyloxymethyl-1H-pyrrolo[2,3-b]pyridin-4-yl)-4-(2-imidazolin-2-yl)aminomethylcyclohexanecarboxamide
(150) trans-N-(1H-pyrrolo[2,3-b]pyridin-4-yl)-4-(3-benzylguanidinomethyl)cyclohexanecarboxamide
(151) trans-N-(1H-pyrrolo[2,3-b]pyridin-4-yl)-4-(3-phenylguanidinomethyl)cyclohexanecarboxamide
(152) trans-N-(1H-pyrrolo[2,3-b]pyridin-4-yl)-4-(3-propylguanidinomethyl)cyclohexanecarboxamide
(153) trans-N-(1H-pyrrolo[2,3-b]pyridin-4-yl)-4-(3-octylguanidinomethyl)cyclohexanecarboxamide
(154) trans-N-(1-benzyloxymethylpyrrolo[2,3-b]pyridin-4-yl)-4-(2-benzyl-3-ethylguanidinomethyl)cyclohexanecarboxamide
(155) trans-N-(1H-pyrrolo[2,3-b]pyridin-4-yl)-4-(imidazol-2-yl)aminomethylcyclohexanecarboxamide
(156) trans-N-(1H-pyrrolo[2,3-b]pyridin-4-yl)-4-(thiazol-2-yl)aminomethylcyclohexanecarboxamide
(157) (R)-(+)-N-(4-pyridyl)-4-(1-aminoethyl)benzamide
(158) N-(4-pyridyl)-4-(1-amino-1-methylethyl)benzamide
(159) N-(4-pyridyl)-4-aminomethyl-2-benzyloxybenzamide
(160) N-(4-pyridyl)-4-aminomethyl-2-ethoxybenzamide
(161) (R)-(−)-N-(4-pyridyl)-4-(1-aminoethyl)-3-nitrobenzamide
(162) (R)-(−)-N-(4-pyridyl)-3-amino-4-(1-aminoethyl)benzamide
(163) (R)-(+)-N-(4-pyridyl)-4-(1-aminoethyl)-3-chlorobenzamide
(164) N-(4-pyridyl)-3-aminomethylbenzamide
(165) (R)-(+)-N-(1H-pyrrolo[2,3-b]pyridin-4-yl)-4-(1-aminoethyl)benzamide
(166) (R)-(+)-N-(1H-pyrazolo[3,4-b]pyridin-4-yl)-4-(1-aminoethyl)benzamide
(167) N-(1H-pyrazolo[3,4-b]pyridin-4-yl)-4-guanidinomethylbenzamide
(168) N-(4-pyridyl)-4-guanidinomethylbenzamide
(169) (R)-(+)-N-(4-pyridyl)-4-(1-aminoethyl)-3-fluorobenzamide
(170) N-(4-pyridyl)-4-aminomethylbenzamide
(171) N-(4-pyridyl)-4-aminomethyl-2-hydroxybenzamide
(172) N-(4-pyridyl)-4-(2-aminoethyl)benzamide
(173) N-(4-pyridyl)-4-aminomethyl-3-nitrobenzamide
(174) N-(4-pyridyl)-3-amino-4-aminomethylbenzamide
(175) (S)-(−)-N-(4-pyridyl)-4-(1-aminoethyl)benzamide
(176) (S)-(−)-N-(4-pyridyl)-2-(1-aminoethyl)benzamide
(177) (R)-(+)-N-(4-pyridyl)-4-(1-aminoethyl)-2-chlorobenzamide
(178) (R)-(+)-N-(1H-pyrrolo[2,3-b]pyridin-4-yl)-4-(1-(3-propylguanidino)ethyl)benzamide
(179) (R)-(−)-N-(1H-pyrrolo[2,3-b]pyridin-4-yl)-4-(1-aminoethyl)-3-azidebenzamide
(180) (R)-(+)-N-(4-pyridyl)-4-(1-aminoethyl)-2-nitrobenzamide
(181) (R)-(−)-N-(4-pyridyl)-4-(1-aminoethyl)-3-ethoxybenzamide
(182) (R)-(+)-N-(3-iodo-1H-pyrrolo[2,3-b]pyridin-4-yl)-4-(1-aminoethyl)benzamide
(183) (R)-(+)-N-(3-iodo-1H-pyrrolo[2,3-b]pyridin-4-yl)-4-(1-aminoethyl)-3-azidebenzamide
(184) (R)-(−)-N-(4-pyridyl)-4-(1-aminoethyl)-3-hydroxybenzamide
(185) N-(1H-pyrazolo[3,4-b]pyridin-4-yl)-4-guanidinomethyl-3-nitrobenzamide
(186) (R)-N-(1H-pyrazolo[3,4-b]pyridin-4-yl)-4-(1-guanidinoethyl)-3-nitrobenzamide
(187) (R)-N-(1H-pyrazolo[3,4-b]pyridin-4-yl)-4-(1-aminoethyl)-2-nitrobenzamide
(188) N-(1H-pyrazolo[3,4-b]pyridin-4-yl)-4-guanidinobenzamide
(189) (R)-N-(1H-pyrazolo[3,4-b]pyridin-4-yl)-4-(1-aminoethyl)-3-nitrobenzamide
(190) (R)-N-(1H-pyrazolo[3,4-b]pyridin-4-yl)-4-(1-guanidinoethyl)benzamide
(191) N-(1H-pyrazolo[3,4-b]pyridin-4-yl)-4-(1-amino-2-hydroxyethyl)benzamide
(192) N-(1H-pyrazolo[3,4-b]pyridin-4-yl)-4-aminomethyl-3-nitrobenzamide
(193) N-(1H-pyrrolo[2,3-b]pyridin-4-yl)-4-piperidinecarboxamide
(194) N-(1H-pyrazolo[3,4-b]pyridin-4-yl)-4-piperidinecarboxamide
(195) N-(1H-pyrazolo[3,4-b]pyridin-4-yl)-1-aminoacetyl-4-piperidinecarboxamide
(196) N-(1-methoxymethyl-1H-pyrazolo[3,4-b]pyridin-4-yl)-4-piperidinecarboxamide
(197) N-(2,3-dihydro-1H-pyrrolo[2,3-b]pyridin-4-yl)-4-piperidinecarboxamide
(198) N-(1H-pyrrolo[2,3-b]pyridin-4-yl)-1-(2-phenylethyl)-4-piperidinecarboxamide
(199) N-(1H-pyrrolo[2,3-b]pyridin-4-yl)-1-amidino-4-piperidinecarboxamide
(200) N-(1H-pyrrolo[2,3-b]pyridin-4-yl)-1-(3-phenylpropyl)-4-piperidinecarboxamide (201) N-(1H-pyrrolo[2,3-b]pyridin-4-yl)-1-benzyl-4-piperidinecarboxamide
(202) N-(1H-pyrazolo[3,4-b]pyridin-4-yl)-1-(2-phenylethyl)-4-piperidinecarboxamide
(203) N-(1H-pyrazolo[3,4-b]pyridin-4-yl)-1-(3-phenylpropyl)-4-piperidinecarboxamide Preferred are compounds (80), (109), (110), (112), (115), (142), (143), (144), (145), (153), (157), (163), (165), (166) and (179).

The compound having a Rho kinase inhibitory activity may be a pharmaceutically acceptable acid addition salt, wherein the acid is exemplified by inorganic acid such as hydrochloric acid, hydrobromic acid, sulfuric acid and the like, and organic acid such as methanesulfonic acid, fumaric acid, maleic acid, mandelic acid, citric acid, tartaric acid, salicylic acid and the like. A compound having a carboxyl group can be converted to a salt with a metal such as sodium, potassium, calcium, magnesium, aluminum and the like, a salt with an amino acid such as lysine and the like. Further, monohydrate, dihydrate, 1/2 hydrate, 1/3 hydrate, 1/4 hydrate, 2/3 hydrate, 3/2 hydrate and the like are encompassed in the present invention.

The compound of the formula (I) can be synthesized by a method described in, for example, JP-A-62-89679, JP-A-3-218356, JP-A-5-194401, JP-A-6-41080, WO95/28387, WO98/06433 and the like.

When the above-mentioned compound having a Rho kinase inhibitory activity has an optical isomer, its racemate or cis- trans isomers, all of them can be used in the present invention. These isomers can be isolated by a conventional method or can be produced using starting materials of the isomers.

A compound having a Rho kinase inhibitory activity, particularly, a compound of the formula (I), an isomer thereof and/or a pharmaceutically acceptable acid addition salt thereof have various actions such as an inhibitory action on the activation of hepatic stellate cell, suppression of fibrogenesis in liver tissue and the like, in mammals inclusive of human, cow, horse, dog, mouse, rat and the like. Therefore, they can be preferably used as an inhibitor of activation of hepatic stellate cell, an agent for the prophylaxis and treatment of liver diseases such as hepatitis, hepatic fibrosis, hepatic cirrhosis, hepatic cancer and the like, or an agent for the prophylaxis and treatment of liver diseases caused by activation of hepatic stellate cell.

When the compound having a Rho kinase inhibitory activity is used as a pharmaceutical, it is produced as a general pharmaceutical preparation and administered orally or parenterally.

For example, the compound having a Rho kinase inhibitory activity is mixed with a pharmaceutically acceptable carrier (e.g., excipient, binder, disintegrator, corrective, corrigent, emulsifier, diluent, solubilizer and the like) to give a pharmaceutical composition or a pharmaceutical preparation in the form of tablet, pill, powder, granule, capsule, troche, syrup, liquid, emulsion, suspension, injection (e.g., liquid, suspension and the like), suppository, inhalant, percutaneous absorber, eye drop, eye ointment and the like in the form suitable for oral or parenteral preparation.

When preparing a solid preparation, additives such as sucrose, lactose, cellulose sugar, D-mannitol, maltitol, dextran, starches, agar, arginates, chitins, chitosans, pectines, tragacanth gum, gum arabic, gelatins, collagens, casein, albumin, calcium phosphate, sorbitol, glycine, carboxymethylcellulose, polyvinylpyrrolidone, hydroxypropylcellulose, hydroxypropylmethylcellulose, glycerol, polyethyleneglycol, sodium hydrogencarbonate, magnesium stearate, talc and the like are used. Tablets can be applied with a typical coating, where necessary, to give sugar coated tablets, enteric tablets, film-coated tablets, two-layer tablets and multi-layer tablets.

When preparing a semi-solid preparation, animal and plant fats and oils (e.g., olive oil, corn oil, castor oil and the like), mineral fats and oils (e.g., petrolatum, white petrolatum, solid paraffin and the like), wax (e.g., jojoba oil, carnauba wax, bee wax and the like), partly or entirely synthesized glycerol fatty acid esters (e.g., lauric acid, myristic acid, palmitic acid and the like), and the like are used.

Examples of commercially available products of these include Witepsol (manufactured by Dynamitnovel Ltd.), Farmazol (NOF Corporation) and the like.

When preparing a liquid preparation, an additive, such as sodium chloride, glucose, sorbitol, glycerol, olive oil, propylene glycol, ethyl alcohol and the like, is used. When preparing an injection, a sterile aqueous solution such as physiological saline, isotonic solution, oil (e.g., sesame oil and soybean oil) and the like are used. Where necessary, a suitable suspending agent such as sodium carboxymethylcellulose, nonionic surfactant, solubilizer (e.g., benzyl benzoate and benzyl alcohol), and the like can be concurrently used. Moreover, when an eye drop is prepared, an aqueous liquid or solution is used, which is particularly a sterile injectable aqueous solution. The eye drop can appropriately contain various additives such as buffer (borate buffer, acetate buffer, carbonate buffer and the like are preferable for reducing irritation), isotonicity agent, solubilizer, preservative, thickener, chelating agent, pH adjusting agent (generally, pH is preferably adjusted to about 6–8.5) and aromatic.

The dose of the compound having a Rho kinase inhibitory activity, which is the active ingredient of these preparations, is 0.1–100 wt %, suitably 1–50 wt %, of the preparation. While the dose varies depending on the symptom, body weight, age and the like of patients, it is generally about 1–500 mg a day for an adult, which is administered preferably once to several times a day.

EXAMPLES

The present invention is explained in detail by referring to Formulation Examples and pharmacological action. The present invention is not limited in any way by the examples.

The method of formulating the preparation of the present invention is explained by referring to Formulation Examples.

The compound used in the present invention is also referred to conveniently as the inventive compound.

Formulation Example 1: Tablet

| | |
|---|---|
| Compound of the present invention | 10.0 mg |
| Lactose | 50.0 mg |
| Corn starch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The compound of the present invention, lactose, corn starch and crystalline cellulose were mixed, kneaded with polyvinylpyrrolidone K30 paste solution and passed through a 20-mesh sieve for granulation. After drying at 50° C. for 2 hours, the granules were passed through a 24-mesh sieve, and talc and magnesium stearate were added. Using a φ07 mm punch, tablets weighing 120 mg per tablet were prepared.

Formulation Example 2: Capsules

| Compound of the present invention | 10.0 mg |
|---|---|
| Lactose | 70.0 mg |
| Corn starch | 35.0 mg |
| polyvinylpyrrolidone K30 | 2.0 mg |
| Talc | 2.7 mg |
| Magnesium stearate | 0.3 mg |
| | 120.0 mg |

The compound of the present invention, lactose and corn starch were mixed, kneaded with polyvinylpyrrolidone K30 paste solution and passed through a 20-mesh sieve for granulation. After drying at 50° C. for 2 hours, the granules were passed through a 24-mesh sieve and talc and magnesium stearate were added. The mixture was filled in hard capsules (No. 4) to give capsules weighing 120 mg.

The pharmacological action of the pharmaceutical agent of the present invention is explained in the following by referring to

EXPERIMENTAL EXAMPLES

In the following Experimental Examples, a compound having a Rho kinase inhibitory activity: (+)-trans-4-(1-aminoethyl)-1-(4-pyridylcarbamoyl)cyclohexane 2HCl.1H$_2$O (hereinafter Y-27632) was used.

Experimental Example 1

Effect on Cell Morphology of Hepatic Stellate Cell

Figure 2:
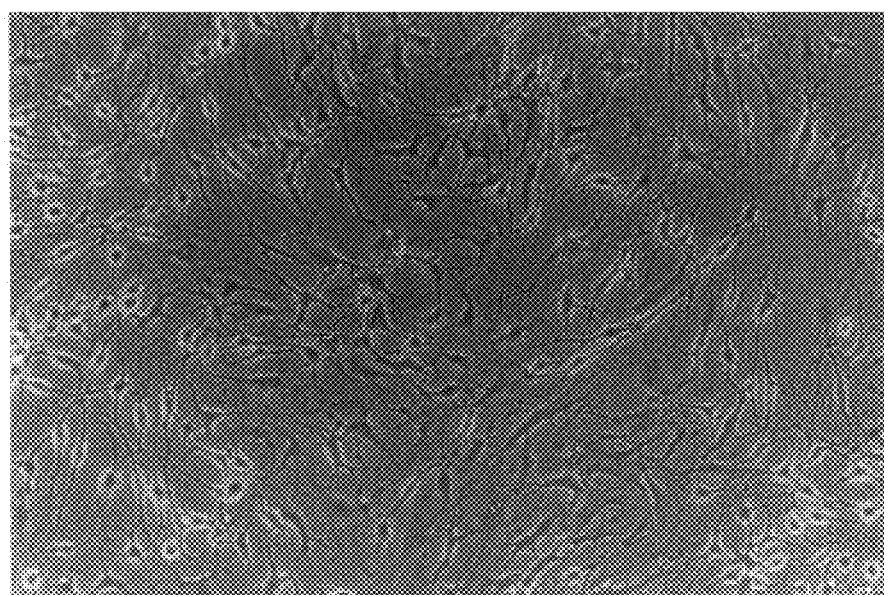
FIG. 2 is a phase contrast microscopic photograph of hepatic stellate cells with the addition of Y-27632.

Hepatic stellate cells (HSC) were prepared from the liver of male Wistar rat according to the method of Friedman et al (Friedman S. L, et al., Proc Natl Acad Sci USA 1985; 82: 8681–8685). HSC were cultured in Dulbecco's modified Eagle's medium (DMEM) containing 20% fetal calf serum (FCS) and the cells after 3 to 8 passages were used. HSC to be subjected to the experiment were sown in a dish treated with fibronectin (10 µg/ml), cultured in DMEM medium containing 20% FCS for 24 hours and changed to DMEM medium containing 1% FCS or DMEM medium containing Y-27632 (30 µM) and 1% FCS. One hour later, HSC were fixed with a 3.7% formaldehyde solution and observed under a phase contrast microscope. As a result, cells were extended (active type) in a medium without Y-27632 but assumed a spindle-like shape with dendroidal protrusions (non-active type) by the addition of Y-27632. The results are shown in FIGS. 1–2.

Experimental Example 2

Effect on Production of Collagen I in Hepatic Stellate Cells

In the same manner as in Experimental Example 1, HSC were prepared from rat liver and cultured in DMEM medium containing 20% FCS for 8 days and changed to DMEM medium without FCS or DMEM medium containing Y-27632 (30 µM) but without FCS. After 48 hours of culture, the amount of collagen I contained in the supernatant was measured by ELISA (enzyme-linked immunosorbent assay) (Moshage H, et al., Hepatology 1990; 12: 511–518). As a result, the amount was 19.5±3.0 µg/µg DNA for the group without Y-27632 and 8.2±2.3 µg/µg DNA for the group with the addition of Y-27632, showing a significant low level for the group with the addition of Y-27632 (p<0.01, n=4).

Experimental Example 3

Effect on Rat with Hepatic Fibrosis Induced by Dimethylnitrosamine (Method)

1% Dimethylnitrosamine (100 µl/100 g rat body weight) was intraperitoneally administered to male Wistar rats for 3 consecutive days per week for 4 weeks (12 times in total) to prepare a hepatic fibrosis model rat. To the Y-27632 administration group, Y-27632 (30 mg/kg) was orally administered every day for 4 weeks from the day when the dimethylnitrosamine administration was started. To the control group, physiological saline was administered. Four weeks later, the liver was removed and the level of fibrogenesis of the tissue, collagen content and hydroxyproline amount were measured.

The level of fibrogenesis was measured as follows. A part of the removed liver was fixed with a formalin solution overnight, and a paraffin embedded piece was prepared and stained by Masson trichrome stain. The stained images were input in a computer through a digital camera (Fujix HC-1000, Fuji Film, Tokyo, Japan) and, using a computer-assisted morphometric analyzer (MacScope, Mitani corporation, Fukui, Japan), the area ratio of the collagen portion stained in bright green was determined as the degree of fibrogenesis.

The amout of tissue collagen was measured as follows according to the method of Shiba et al. (Shiba M, et al. Liver, 1998, Jun; 18(3): 196–204). That is, a part of the removed liver was homogenized with a 33-fold amount (ml/g) of 0.5M aqueous acetic acid solution in a Polytron PCU-2 homogenizer (Kinematica, Luzern, Switzerland). The homogenate was subjected to ultrasonication treatment for 2 min after freeze-thawing. After extraction with an acid, a fraction containing insoluble collagen was heated at 80° C. for 60 minutes to convert the insoluble collagen to water-soluble gelatin. The amount of gelatin was measured with a Sircol collagen assay kit (Biocolor, Belfast, Northern Ireland).

The amount of hydroxyproline was measured as follows. A part of the removed liver was homogenized with a 10-fold amount (ml/g) of physiological saline in a Polytron PCU-2 homoginizer (Kinematica, Luzern, Switzerland). The amount of hydroxyproline was measured according to the method of Fujiwara et al. (Fujiwara et al., Anal. Biochem., 1987; 166: 72–8) with a high performance liquid chromatography system (SRL Inc., Tachikawa, Japan).

(Results)

The level of fibrogenesis was 13.4±2.3% for the control group (4 rats) but 6.3±0.7% for the Y-27632 administration group (5 rats) (p<0.05 by Mann-Whiteney significance test), showing significant suppression of fibrogenesis by the administration of Y-27632. The content of collagen in the tissue was 808.5±122.4 µg/100 mg-rat liver weight for the control group (4 rats) and 601.3±67.7 µg/100 mg-rat liver weight for the Y-27632administration group (5 rats) (p<0.05 by Mann-Whiteney significance test), showing significant lowering of tissue collagen content by the administration of Y-27632. The content of hydroxyproline in the tissue was 59.5±14.1 µmol/g-rat liver weight for the control group (4 rats) and 29.8±9.1 µmol/g-rat liver weight for the Y-27632 administration group (5 rats) (p<0.05 by Mann-Whiteney significance test), showing significant lowering of tissue hydroxyproline content by the administration of Y-27632.

Figure 3:
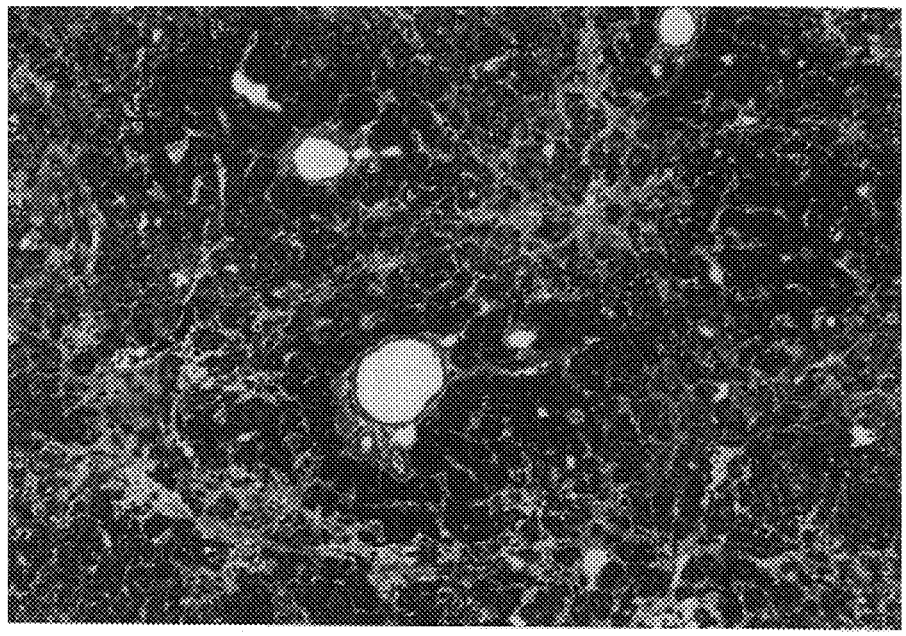
FIG. 3 shows an exemplary photograph of rat (control group) liver tissue stained by Masson trichrome stain.
Figure 4:
FIG. 4 shows an exemplary photograph of rat (Y-27632 administration group) liver tissue stained with Masson trichrome stain.

The photographs of tissues stained by Masson trichrone stain are shown in FIGS. 3–4.

Industrial Applicability

From the above-mentioned Formulation Examples and pharmacological tests, it is evident that the compound having a Rho kinase inhibitory activity is useful as an activation inhibitor of hepatic stellate cells and as an agent for the prophylaxis and treatment of liver diseases, such as hepatitis, hepatic fibrosis, hepatic cirrhosis, hepatic cancer and the like, because it inhibits activation of hepatic stellate cells and suppresses hepatic fibrogenesis in animal models of hepatic fibrosis.

This application is based on a patent application No. 120624/1999 filed in Japan, the contents of which are all hereby incorporated by reference.

What is claimed is:

1. A method of the prophylaxis or treatment of liver disease caused by activation of hepatic stellate cells, which comprises administering a pharmaceutically effective amount of an amide compound of the following formula (I)

$$Ra-\underset{\underset{}{\overset{O}{\|}}}{C}-\underset{\underset{Rc}{|}}{\overset{Rb}{\overset{|}{N}}}-Rc \quad (I)$$

wherein

Ra is a group of the formula (a) [structure with R, R¹, N, A, cyclohexane with R²]
or
(b) [structure with R, R¹, N, A, phenyl with R³, R⁴]

in the formulas (a) and (b),

R is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula $$-(CH_2)_l(\underset{\underset{R^{11}}{|}}{\overset{R^{10}}{\overset{|}{C}}})_m(CH_2)_n- \quad (e)$$

wherein $R^{10}$ and $R^{11}$ are the same or different and each is hydrogen or alkyl, and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof, to a patient in need thereof.

2. The method of claim 1, wherein the amide compound is an amide compound of the following formula (I')

$$Ra'-\underset{\underset{}{\overset{O}{\|}}}{C}-\underset{\underset{Rc}{|}}{\overset{Rb}{\overset{|}{N}}}-Rc \quad (I')$$

wherein

Ra' is a group of the formula (a') [structure with R', R¹, N, A, cyclohexane with R²]
or
(b') [structure with R', R¹, N, A, phenyl with R³, R⁴]

wherein

R' is hydrogen, alkyl, or cycloalkyl, cydoalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula $$-(CH_2)_l(\underset{\underset{R^{11}}{|}}{\overset{R^{10}}{\overset{|}{C}}})_m(CH_2)_n- \quad (e)$$

wherein $R^{10}$ and $R^{11}$ are the same or different and each is hydrogen or alkyl, and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

3. The method of claim 1, wherein the amide compound is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

4. The method of of claim 1, wherein the amide compound is a (+)-trans-4-(1-aminoethyl)-1-(4-pyridylcarbamoyl)cyclohexane, and/or a pharmaceutically acceptable acid addition salt thereof.

5. The method of claim 1, wherein the liver disease is at least one selected from the group consisting of hepatitis, hepatic fibrosis, hepatic cirrhosis and hepatic cancer.

6. A method for inhibiting activation of hepatic stellate cells, which comprises administering a pharmaceutically effective amount of an amide compound of the following formula (I)

   (I)

wherein

Ra is a group of the formula

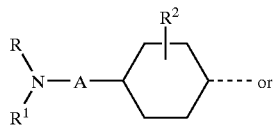   (a)

or

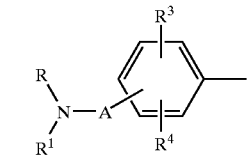   (b)

in the formulas (a) and (b),

R is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, A is a group of the formula

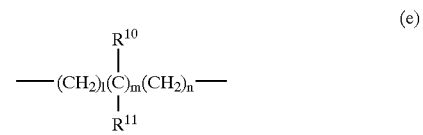   (e)

wherein $R^{10}$ and $R^{11}$ are the same or different and each is hydrogen or alkyl, and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof, to a patient in need thereof.

7. The method of claim 6, wherein the amide compound is an amide compound of the following formula (I')

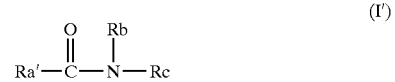   (I')

wherein

Ra' is a group of the formula

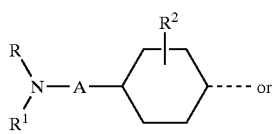   (a)

or

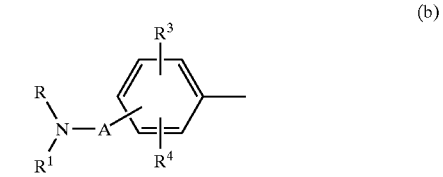   (b)

wherein

R' is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

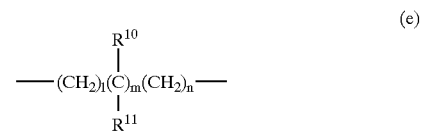   (e)

wherein $R^{10}$ and $R^{11}$ are the same or different and each is hydrogen or alkyl, and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

8. The method of claim 6, wherein the amide compound is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof.

9. The method of claim 6, wherein the amide compound is a (+)-trans-4-(1-aminoethyl)-1-(4-pyridylcarbamoyl)cyclohexane, and/or a pharmaceutically acceptable acid addition salt thereof.

* * * * *